United States Patent
Knox, Jr.

(10) Patent No.: US 10,271,556 B2
(45) Date of Patent: Apr. 30, 2019

(54) LIQUIDAMBAR DERIVED CLEANERS

(71) Applicant: G. Richard Knox, Jr., Jacksonville, FL (US)

(72) Inventor: G. Richard Knox, Jr., Jacksonville, FL (US)

( * ) Notice: Subject to any disclaimer, the term of this patent is extended or adjusted under 35 U.S.C. 154(b) by 751 days.

(21) Appl. No.: 14/283,861

(22) Filed: May 21, 2014

(65) Prior Publication Data

US 2015/0335032 A1  Nov. 26, 2015

(51) Int. Cl.

| | |
|---|---|
| *A61K 36/00* | (2006.01) |
| *A01N 65/08* | (2009.01) |
| *A61K 36/185* | (2006.01) |
| *A61K 8/97* | (2017.01) |
| *C11D 1/00* | (2006.01) |
| *A61Q 11/00* | (2006.01) |
| *A61Q 5/02* | (2006.01) |
| *A61Q 19/10* | (2006.01) |
| *A61L 9/14* | (2006.01) |
| *C11D 3/382* | (2006.01) |
| *C11D 7/44* | (2006.01) |

(52) U.S. Cl.
CPC ............... *A01N 65/08* (2013.01); *A61K 8/97* (2013.01); *A61K 36/185* (2013.01); *A61L 9/14* (2013.01); *A61Q 5/02* (2013.01); *A61Q 11/00* (2013.01); *A61Q 19/10* (2013.01); *C11D 1/00* (2013.01); *C11D 3/382* (2013.01); *C11D 7/44* (2013.01)

(58) Field of Classification Search
CPC ........................................................ A61K 36/00
See application file for complete search history.

(56) References Cited

FOREIGN PATENT DOCUMENTS

| CN | 101518610 A | * | 9/2009 |
| CN | 102327485 A | * | 1/2012 |

* cited by examiner

*Primary Examiner* — Qiuwen Mi
(74) *Attorney, Agent, or Firm* — Steven R. Scott

(57) ABSTRACT

The present invention is a surfactant(s) for use as a cleaner and freshener as well as methods for the production/use of such surfactants/cleaners/fresheners. The surfactant is produced using and relying upon properties of the *Liquidambar* tree, particularly the *Liquidambar* leaf, by creating a liquid solution useful for cleaning and freshening purposes by soaking or steeping the leaves of *Liquidambar* in a solvent, preferably water. The solutions formed have been found to be effective for general cleaning and freshening purposes including, but not limited to, all known household cleaning/freshening purposes as well as for personal bodily cleaning/freshening purposes including, but not limited to, body washing, hair washing, tooth brushing, mouth washing, and the like. It is non-allergenic, non-toxic, and will cause no adverse environmental effects.

11 Claims, 1 Drawing Sheet

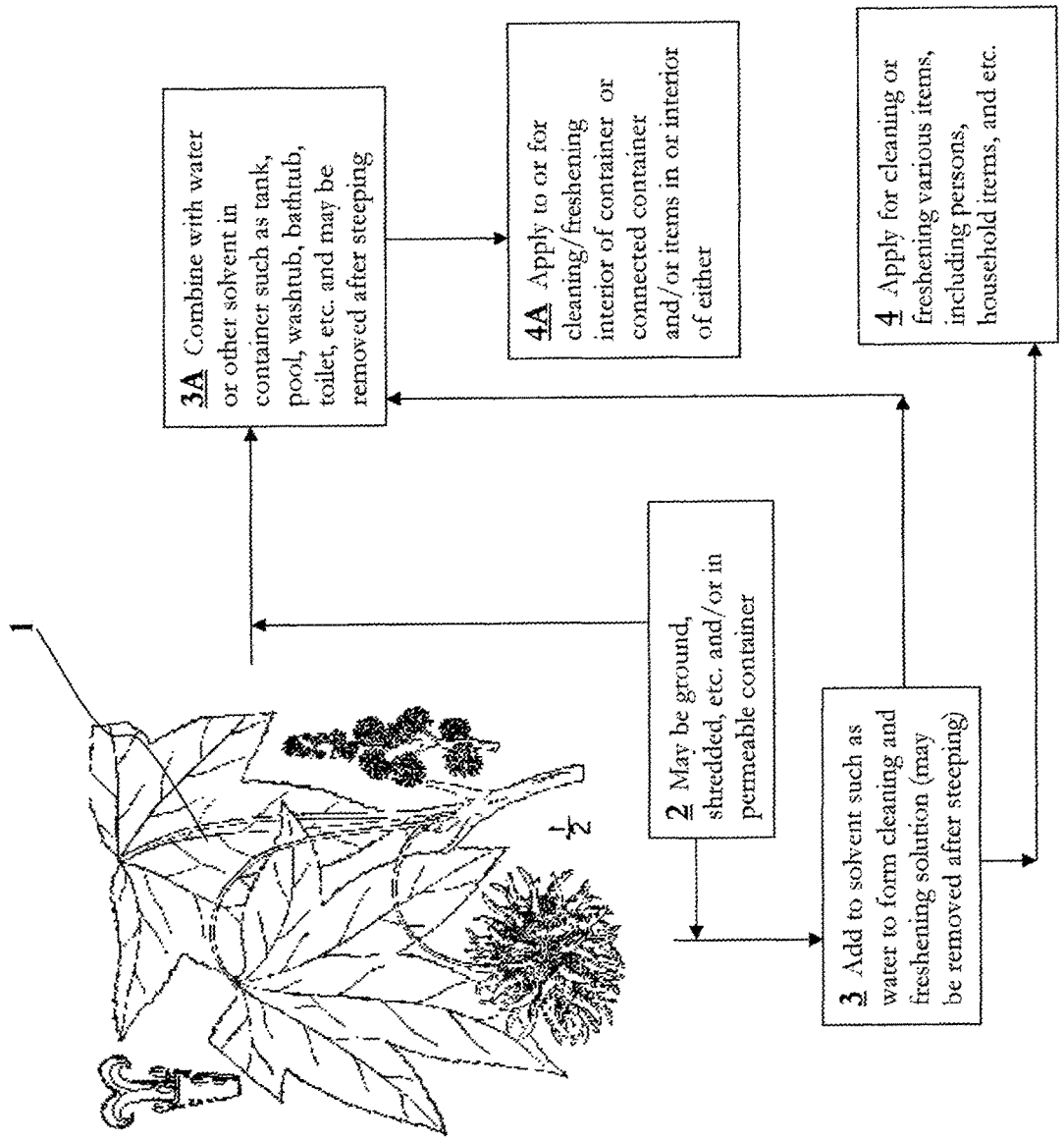

LIQUIDAMBAR DERIVED CLEANERS

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO MICROFICHE APPENDIX

Not Applicable.

BACKGROUND OF THE INVENTION

Field of the Invention

The present invention relates to surfactant(s) for use as cleaners (and/or fresheners) as well as novel methods for the production/use of said surfactants/cleaners. More specifically, the invention pertains to surfactant(s) for use as cleaners/fresheners that are produced from and/or using the leaf of the Sweetgum (*Liquidambar*) tree, and the formulation, method of production, and method of using such surfactants and cleaners/fresheners.

Relevant Art

Surfactants include compounds that lower the surface tension between two liquids or between a liquid and a solid, including detergents, emulsifiers (which serve to emulsify—e.g., fats and oils in water), foaming agents (such as soaps) that facilitate formation of foam, and dispersants. Generally, Surfactants are organic compounds that are amphiphilic, meaning they contain both hydrophobic groups (referred to as their "tails") and hydrophilic groups (referred to as their "heads"). Therefore, a surfactant includes both water insoluble (i.e., oil soluble) components and water soluble components. Consequently, surfactants will diffuse in water and adsorb at interfaces between air and water or at the interface between oil and water (in the case of water mixed with oil).

A detergent is a surfactant or a mixture of surfactants with cleaning properties in dilute solutions. These substances are compounds that are similar to soap but are more soluble in hard water, including for household purposes laundry detergent and dish detergent as opposed to hand soap or other types of cleaning agents. Detergents, like soaps and other surfactants, work because they are amphiphilic, i.e., partly hydrophilic and partly hydrophobic. Their dual nature facilitates the mixture of hydrophobic compounds (like oil and grease) with water. Because air is not hydrophilic, detergents are also foaming agents to varying degrees. This quality is especially evident in dish washing detergents, which are usually comprised of high-foaming mixtures of surfactants with low skin irritation. Other surfactants include soaps used for washing, bathing and cleaning, (including shampoos and bar soaps), and dispersants. Even stronger cleaning solutions, such as those used on hard surfaces, are typically formed using concentrated solutions of surfactants (such as detergents) and water softeners, which enhance and improve the action of the surfactant in hard water.

Unfortunately, the surfactants commonly used to form the useful cleaning compounds and substances of prior art often have undesirable qualities. For example, many may be allergenic, unhealthy for humans and animals, and/or cause adverse environmental effects. One of the most well known examples of the latter is the problems caused by the use of phosphates in soaps and detergents. Phosphates improve the cleaning efficiency of soaps and detergents; especially in areas with "hard" water that contain excessive amounts of calcium and magnesium. However, the strong cleaning performance of phosphates is also coupled with extremely adverse consequences for rivers, lakes, streams, and other fresh waters. Levels of phosphates in such fresh water bodies is often much higher than normal due contamination from municipal and domestic waste water with soaps and detergents containing phosphates. Since phosphates encourage the growth of algae, they lead not only to such waters smelling bad, being unpleasant to swim in or look at, and unsuitable for drinking, but to—in the long range—the acceleration of eutrophication, where water bodies fill in with dead algae and other organic matter and eventually turn into dry land.

As previously noted, environmental and other problems clearly exist in the case of current surfactants used for cleaning, whether at a personal/individual level such as soaps and shampoos; a household cleaning level such as laundry detergents, dish washing detergents, and household cleaners; and/or at a more heavy duty or institutional level. These problems as well as an increasing personal and cultural drive to use natural substitutes in place of more artificially derived and manufactured surfactant consumer products has led to a host of new "green" products that have enjoyed, and can be used with, only limited success. An unexpected source of such has been discovered and developed by the inventor based on unexploited and unknown qualities of a common and even sometimes despised tree. The *Liquidambar* tree, and in particular the most common American species thereof. *Liquidambar Styracilua* (commonly known as the "Sweetgum" or "American Sweetgum"), is a familiar feature in the Southeastern United States. It is a deciduous tree native to warm temperate areas and is one of the main forest trees of the Southeastern United States. It is easily recognizable by its five-pointed star shaped leaves and hard spiky fruit. This fruit or seed is often considered a "pesky" byproduct of an otherwise attractive tree, causing it to be considered by many to be "trash" or "pest" tree for yards and landscaping purposes.

Nonetheless, the Sweetgum tree does have known uses. In the carpentry industry, the timber of the Sweetgum is important in the manufacture of plywood. It is also used for furniture, interior trim, railroad ties, cigar boxes, crates, flooring, barrels, woodenware, and wood pulp. The tree's gum resin, for which the tree is named, exudes from the bark of the tree when cut, abraded, or otherwise broken. This resin has many names including liquid amber. It may be clear, reddish, or yellow, and has a smell that is generally considered to be pleasant. It has long been believed that the gum and even sometimes the bark from the tree has medicinal properties and these parts of the tree are represented as such in folklore and older pharmaceutical publications. More recently, it has been determined that shikimic acid, a key ingredient in the production of Tamiflu, an anti-viral medication, can be usefully extracted from the seeds of the Sweetgum, though it is present in the seeds in far lower concentrations than are found in its usual source, the Chinese Star Anise. It is likewise found in small amount in the leaves of the Sweetgum.

Notwithstanding the uses found for other parts of the Sweetgum, the leaves of the Sweetgum have not previously seen substantial usage in any significant way, though there are some reports that certain American Indian tribes used the leaves, after soaking or boiling, for medicinal poultices and may have mixed them with tobacco for smoking. Likewise, one historic source dating to 1863 stated that the leaves of the Sweetgum "when green . . . [are] powerfully astringent . . . contain as large a proportion of tannin as that of any other tree [and can] be used whenever an astringent is required . . . cold water takes it up [and it can also be used] for tanning leather . . . "

However, some interest has more recently been shown in the possible pharmaceutical uses of the leaves of *Liquidambar*. As well as normally expected chlorophyll and foliar nutrients (including nitrogen, potassium, calcium, phosphorus and magnesium), it has been found that leaf oil from this species obtained by simultaneous distillation extraction and analyzed in a 1989 study contained thirty-six notable components, all terpenoid. Terpenoids are lipids that can be found in all living things and constitute a large group of natural products. Plant terpenoids, in particular, are used extensively for their aromatic qualities (contributing to, e.g., the scent of eucalyptus, and the flavors of cinnamon, cloves and ginger).

The major Terpenoid constituents for *Liquidambar* were found by this study to be terpinen-4-ol, alpha-pinene and sabinene. Terpinen-4-ol is considered to be the primary active ingredient of tea tree oil and is also the compound of highest concentration in the essential oil of nutmeg. Alpha-pinene is found in the oils of many conifers, including pine. It also occurs in the essential oil of rosemary. Sabinene is one of the chemical compounds that contributes to the spiciness of black pepper. It is found in carrot seed oil as well as occurring in low concentration in tea tree oil. The study concluded that the "high terpinen-4-ol and low 1,8-cineole content make the oil of some pharmacological interest."

Nonetheless, as far as can be determined, the bark, wood and gum of the Sweetgum have not seen any usage for, or inclusion in, cleaning/freshening products. This observation is even more unassailable in the case of the leaves of the Sweetgum, which (a) despite the study cited noting possible pharmaceutical uses have almost no record whatsoever of having a useful purpose in any area of prior art, and (b) more particularly, have no record of being used for cleaning/freshening purposes and/or in the production of, or for, cleaning/freshening products.

SUMMARY OF THE INVENTION

As previously stated, the present invention relates to surfactant(s) for use as cleaners/fresheners as well as novel methods for the production/use of said surfactants. In one aspect of the present invention there is provided an easily manufactured surfactant which, in various concentrations, can be used for various cleaning/freshening purposes. Another aspect of the invention is the provision of this surfactant using and relying upon properties of the *Liquidambar* and particularly the *Liquidambar* leaf not previously suspected of having utility for cleaning/freshening purposes and/or used for cleaning/freshening purposes. Still another aspect of the current invention is/are the method and methods by which such a surfactant/cleaner is produced, produced in various concentrations for various purposes, and used. In the preferred embodiments of the invention discussed below, all of the foregoing inventive aspects are realized by creating a liquid solution useful for cleaning purposes by soaking or steeping the leaves of *Liquidambar* in a solvent, preferably water, for the purposes of the invention. In general, the proportions of leaves to water determine the relative strength of the solution formed and, thereby, its ideal purposes for cleaning purposes. The cleaners/fresheners formed have been found to be non-allergenic, non-toxic, and will cause no adverse environmental effects. In addition, with regard to environmental effects, it should be noted that the shed leaves of *Liquidambar* form a normal part of the ecosystems where these trees grow, are subject to natural steeping as part of the leaf detritus forming part of the swamps and watersheds through their natural ranges, and are not considered in any way to be harmful to the environment in this role.

BRIEF DESCRIPTION OF THE DRAWINGS

The novel features believed to be characteristic of this invention are set forth with particularity in the appended claims. The invention itself, however, both as to its organization and method of operation, together with further object and advantages thereof, may be better understood by reference to the following description taken in connection with the accompanying drawings in which:

FIG. 1 provides a schematic diagram illustrating in general fashion the process for producing and applying the products of my invention.

DESCRIPTION

The present invention relates to cleaners/fresheners and/or surfactant(s) for use as cleaners/fresheners as well as novel methods for the production/use of said surfactants/cleaners. Several examples of the production and use of such surfactants/cleaners are set forth below.

First Examples

Variable amounts and numbers of *Liquidambar* leaves 1 were added to and as part of a standard washing machine wash cycle in place of any type of commercially available detergent (See, 3A and 4A). It was found that clothing washed in this way (See, 3A and 4A) was effectively cleaned and deodorized by the *liquidambar* leaves 1, with the valuable factors present in said leaves 1 apparently being released in the wash water during the initial wash cycle and the remains of the *Liquidambar* leaves 1 being removed thereafter by and during the remaining parts of the wash and rinse cycles of the washing machine (See, 3A and 4A). Likewise, any tannin or other potentially staining components released were effectively removed during the wash and rinse cycles and did not create tinting of staining of clothing. In addition, it was found that the clothing washed in this manner did not create the allergic reactions previously experienced by a sensitive individual in using commercially available clothes washing compounds. Moreover, a fresh pleasing odor was imparted to the items cleaned. (See, 4A)

Thus, it is clear that a method wherein a washing machine provides water as the solvent as part of the washing machine cycle to form the liquid cleaning solution, will clean items placed in the washing machine for cleaning. This result is applicable for all types of washing machines, including but not limited to common clothes washing machines and dish washing machines. A further experiment involved the use of *Liquidambar* leaves 1 for toilet cleaning where the toilet tank provides water as part of the flushing cycle to form the liquid cleaning solution (See, 3A and 4A). The solution generated was thereby applied both to the interior of the toilet tank and to the bowl during flushing for cleaning purposes (See, 3A and 4A). This method also succeeded in cleaning and deodorizing the toilet and tank (See, 4A). From these examples it is clear that a water permeable mesh or fabric container (See, 2) can be provided to contain *Liquidambar* leaves 1 for inclusion in either a washing machine wash cycle or in a toilet tank to accomplish the same goals (See, 3A and 4A). Likewise, it is clear that the method described can be extended to use of *Liquidambar* leaves 1 for cleaning in any type of container or tank of water or similar solvent. Consequently, *Liquidambar* can also be used for cleaning swimming pools, in which case leaves 1 can be placed directly into the water to be swept into the filter baskets for the pool as part of its normal cycle of water circulation, placed directly into the baskets used to filter and remove pool detritus as part of said cycle, or (once again) placed into water permeable pouch or container in either location for the same purpose. (See, 2, 3A and 4A). Alternately, liquid solution 3 can be used for this same purpose. (See, 3, 3A, and 4A). *Liquidambar* leaves 1 or solution 3 would take the place of Chlorine or iodine type cleaners for this purpose.

Second Examples

In order to determine the proportions of *Liquidambar* leaves 1 to use in water for washing in accordance with the method of the FIRST EXAMPLE using a standard washing machine and cycle, different numbers of *Liquidambar* leaves 1 were allowed to steep in water in order to determine the number necessary to be used for effective washing purposes and also to confirm that the solution 3 derived from steeping *Liquidambar* leaves 1 was equally effective for such washing purposes. It was determined that 15 *Liquidambar* leaves 1 allowed to steep in a gallon of water would produce an effective clothes washing solution 3 within approximately 10 minutes by steeping at ordinary room temperatures without heating of the liquid involved, and that ½ cup of the solution 3 so produced was effective in washing a standard load of laundry as described in the FIRST EXAMPLE and with similar cleaning, deodorizing and non-allergenic effects. (See, 3, 3A and 4A). It was noted that liquid 3 produced in this process was—when steeping continued over an extended period—brown in color as is typical of "teas" produced by steeping (with or without heating and boiling) and generally indicative of the presence of tannic acid in such solutions. However, it was found that the solution 3 remained effective with a much shorter period of steeping (approximately 15-20 minutes) and did not assume a brownish color (which might concern consumers by raising concerns about the possibility of staining surfaces or fabrics). In addition, the solution 3 was aromatic in the manner typical of *Liquidambar*. When shaken in a closed container, very mild foaming was noted, possibly indicating the presence of small amounts of foaming compounds such as saponins, though there has been no previous indication of such compounds in *Liquidambar* leaves 1. Further, no notable difference was found (in terms of the purpose of this invention) when fresh green *Liquidambar* leaves 1 as opposed to dried *Liquidambar* leaves 1 were used. The liquid cleaner obtained was also used experimentally in various strengths for various household and personal cleaning tasks with successful results in terms of cleaning deodorizing/freshening.

Third Examples

In order to determine the utility of the cleaning solution 3 previously described for other common/household cleaning tasks, it was thereafter applied and/or used at full strength or in diluted form for a variety of common and household cleaning tasks with great success. In this regard, it was found that the solution 3 derived was not only successful for clothes washing, but was also successful for washing dishes, mopping floors, cleaning windows, cleaning carpet, cleaning bed surfaces, cleaning curtains, cleaning bathroom fixtures and features, eliminating mold and mildew, cleaning ovens, cleaning dust and other grime from tables and other surfaces, cleaning refrigerators, washing cars, cleaning auto interiors, sanitizing air conditioning vents in cars and houses, cleaning garbage cans, and for various and sundry other standard or household cleaning purposes. In all cases, the described solution 3 was found to not only be effective as a cleaner, but non-allergenic, deodorizing, effective as a "freshener," and by virtue of its elimination of mold, mildew and other toxic growths, effective as a general disinfectant. (See, 3 and 4). However, it was also found that for some of the tasks and purposes described it was not necessary to use the full strength solution 3 derived from 15 leaves 1 per gallon of water proportions. Generally, for more intense and unsanitary tasks and cleaning chores, especially those involving hard and impermeable surfaces, such as garbage cans, bathroom fixtures, tile floors, stove cleaning and the like, a full strength solution 3 was warranted. However, for other cleaning processes such as the general cleaning of hard or impermeable surfaces such as counter tops, refrigerators, and the like which were not particularly grimy or unclean, a weaker solution 3 can be utilized. Likewise, for permeable/cloth surfaces and materials such as carpets, rugs and the like, a still weaker solution 3 may be suitable.

Fourth Examples

In order to determine the utility of the cleaning solution 3 previously described for personal cleaning tasks, it was thereafter applied and/or used in even more diluted form for a variety of personal cleaning and hygiene related tasks with great success. In this regard, it was found that solutions 3 derived from steeping *Liquidambar* leaves 1 in water were not only successful and effective when used for bathing the body, but also for shampooing hair, brushing the teeth, use as a mouthwash, gargling, and cleaning infected areas with positive effects thereon including the lessening and/or elimination of infection including athletes foot infections and the like. (See, 3 and 4). In all cases, the described solution 3 was found to not only be effective as a cleaner, but non-allergenic, deodorizing, freshening and by virtue of its effect in the alleviation of fungal infections and other bodily irritations and infections obviously possessing beneficial properties as a topical antiseptic, antibiotic and/or antifungal cleaner and "wash" as well as being soothing and non-allergenic. (See, 3 and 4).

As a result of the foregoing experiments, it was found that *Liquidambar* cleaning solutions 3 in accordance with the teachings of my invention can be successfully used for cleaning and shampooing hair, rinsing hair, cleaning and washing body surfaces, and rinsing body surfaces. (See, 4). Likewise, it was evident that the solution 3 has utility for general topical cleaning of the epidermis, washing wounds, topical cleaning of acne, topical cleaning of rashes and areas of epidermal irritation, and topical cleaning and washing of areas of bacterial and fungal infection of the epidermis. (See, 4). Moreover, the experiments in the mouth and throat established that *Liquidambar* solutions 3 of the invention had utility for throat hygiene by gargling, mouth and teeth hygiene as a mouthwash, tooth cleaning as a tooth brushing solution 3, and via syringe at or beneath the gum for cleaning of the gingival margin (which has proved effective in treating periodontal disease). (See, 4). Finally, the mild, beneficial and non-irritating affects of the *Liquidambar* solutions 3 on the mucosal membranes of the mouth and throat establish its general utility and potential usefulness in and for other such membranes and orifices of the body, establishing its usefulness for ear washing or irrigation, eye washing or irrigation, nasal cleaning or irrigation, vaginal douche, and rectal irrigation or enema. (See, 3 and 4).

Fifth Examples

In order to better determine the optimal strength of solution 3 for different tasks, various strengths were experimentally used for the different purposes outlined in the prior EXAMPLES. It was found that, in general, solutions 3 created in the following manners were suitable for the purposes indicated: (1) for washing clothes—½ cup of a solution 3 produced by steeping 15 leaves 1 in a gallon of water will wash a standard load of clothing in an automatic washing machine for 32 loads per gallon (See, 3, 3A, and 4A); (2) for topical personal hygiene use such as for shampooing/rinsing hair and/or body, etc.—18 oz. water and 1 leaf form a solution 3 of sufficient strength (with the leaf being capable of producing a viable solution 3 for this purpose for up to 10 water refills (See, 3 and 4); (3) for oral hygiene use such as for mouthwash, gargling and the like—3 leaves 1 per ½ gallon of water (See, 3 and 4); (4) for a spray solution 3 for general household cleaning purposes such as cleaning refrigerators, windows, ovens, bathtubs, floors, carpets, mattresses and the like—add ¼ to ½ cup of the washing solution 3 derived in (1) above to a quart container and fill the remainder with water (See, 3 and 4); and (5) for cleaning toilets—½ cup of the same washing solution 3 can be added to bowl or tank (See, 3, 3A, and 4A).

In all cases it has been found that the cleaner/freshener of the invention initially produced an unpleasant odor when applied and then, shortly thereafter, this odor was succeeded and eliminated by a new fresh odor redolent of the aromatic qualities of the *Liquidambar* leaf previously described. Hence, it has also been found that the solution 3 can be used as a general freshener to be misted on fabrics using an appropriate spray container (See, 4) and other items as well as being similarly misted and used for an air freshener (See, 4). In view of the foregoing, it should be clear that numerous changes and variations can be made without exceeding the scope of the inventive concept outlined. Accordingly, it is to be understood that the embodiment(s) of the invention herein described is/are merely illustrative of the application of the principles of the invention. Reference herein to details of the illustrated embodiment(s) is not intended to limit the scope of the claims, which recite those features regarded as essential to the invention.

I claim:

1. A method of cleaning, comprising:
processing some portion of the *Liquidambar* tree to form a cleaning material;
applying the material to an item to be cleaned; and
wherein at least one of: the process includes steeping said portion in a solvent to form a liquid cleaning solution, the portion comprises leaves of the *Liquidambar* tree, the solvent is water, the solvent and portion is combined together in a liquid container where the item is cleaned, and the solvent and portion is combined together in a liquid container and applied to an item to be cleaned which is outside of the container.

2. The method of claim 1, wherein the liquid cleaning solution is produced by at least one of: steeping *Liquidambar* leaves in water to form a liquid cleaning solution, steeping *Liquidambar* leaves in a permeable container in water to form a liquid cleaning solution, steeping parts of *Liquidambar* leaves in water to form a liquid cleaning solution, and steeping parts of *Liquidambar* leaves in a permeable container in water to form a liquid cleaning solution.

3. The method of claim 2, wherein a washing machine provides water as the solvent as part of the washing machine cycle to form the liquid cleaning solution, and the items cleaned are those placed in the washing machine for cleaning.

4. The method of claim 2, wherein a pool provides water as the solvent as part of the water circulating cycle of the pool to form the liquid cleaning solution, and the items cleaned are portions of the pool in contact with said liquid cleaning solution.

5. The method of claim 2, wherein a toilet tank provides water as part of the flushing cycle to form the liquid cleaning solution, and the solution is applied thereby both to the interior of the toilet tank and to the bowl during flushing for cleaning purposes.

6. The method of claim 2, wherein the cleaning solution is applied for at least one of: cleaning and shampooing hair, rinsing hair, cleaning and washing body surfaces, and rinsing body surfaces.

7. The method of claim 2, wherein the cleaning solution is applied for at least one of: topical cleaning of the epidermis, washing wounds, topical cleaning of acne, topical cleaning of rashes and areas of epidermal irritation, and topical cleaning and washing of areas of bacterial and fungal infection of the epidermis.

8. The method of claim 2, wherein the cleaning solution is applied for at least one of: throat hygiene by gargling, mouth and teeth hygiene as a mouthwash, tooth cleaning as a tooth brushing solution, and via syringe beneath at or beneath the gum for cleaning of the gingival margin.

9. The method of claim 2, wherein the cleaning solution is applied for at least one of: ear washing or irrigation, eye washing or irrigation, and nasal cleaning or irrigation.

10. The method of claim 2, wherein the cleaning solution is applied for at least one of: vaginal douche, and rectal irrigation or enema.

11. The method of claim 2, wherein the cleaning solution is applied for at least one of: washing dishes, washing clothes, cleaning fibrous materials, cleaning impermeable materials, cleaning permeable materials, freshening clothes, freshening fibrous materials, freshening impermeable materials, and freshening permeable materials.

\* \* \* \* \*